(12) United States Patent
Gross et al.

(10) Patent No.: US 7,077,800 B2
(45) Date of Patent: Jul. 18, 2006

(54) CABLE ATTACHMENT FOR A RADIOACTIVE BRACHYTHERAPY SOURCE CAPSULE

(75) Inventors: Ian G Gross, Clinton, TN (US); Larry A Pierce, Kingston, TN (US)

(73) Assignee: UT Battelle, LLC, Oak Ridge, TN (US)

( * ) Notice: Subject to any disclaimer, the term of this patent is extended or adjusted under 35 U.S.C. 154(b) by 0 days.

(21) Appl. No.: 10/941,130

(22) Filed: Sep. 15, 2004

(65) Prior Publication Data

US 2006/0058568 A1    Mar. 16, 2006

(51) Int. Cl.
*A61N 5/00* (2006.01)
(52) U.S. Cl. .............................. 600/3; 403/274; 29/505
(58) Field of Classification Search .............. 600/9–15; 403/274, 282, 285; 29/505, 515–517, 282; 385/69, 87; 174/84 C; 439/421
See application file for complete search history.

(56) References Cited

U.S. PATENT DOCUMENTS

| 4,861,520 | A | | 8/1989 | Van't Hooft et al. |
| 5,624,372 | A | * | 4/1997 | Liprie ............................ 600/3 |
| 6,352,500 | B1 | | 3/2002 | Halpern |
| 2003/0204126 | A1 | * | 10/2003 | Rivard ........................... 600/3 |
| 2005/0192708 | A1 | * | 9/2005 | Bertini ......................... 700/265 |

* cited by examiner

*Primary Examiner*—John P. Lacyk
(74) *Attorney, Agent, or Firm*—James M. Spicer; Joseph A. Marasco

(57) ABSTRACT

In cancer brachytherapy treatment, a small californium-252 neutron source capsule is attached to a guide cable using a modified crimping technique. The guide cable has a solid cylindrical end, and the attachment employs circumferential grooves micromachined in the solid cable end. The attachment was designed and tested, and hardware fabricated for use inside a radioactive hot cell. A welding step typically required in other cable attachments is avoided.

7 Claims, 1 Drawing Sheet

CABLE ATTACHMENT FOR A RADIOACTIVE BRACHYTHERAPY SOURCE CAPSULE

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of Invention

The invention relates to radioactive brachytherapy sources, and more particularly to the fabrication of small diameter brachytherapy source capsules having a very high strength guide cable attachment.

2. Description of Prior Art

Brachytherapy is a method of treating cancer in which radioactive sources are placed within the body at the site of the tumor. In one common form of brachytherapy, a capsule containing a radioactive source is removably positioned at the tumor site. This is a standard treatment method using photon or gamma sources as, for example, in high dose rate (HDR) gamma therapy using tiny iridium-192 radioactive sources.

In order to carry out such treatment methods, a thin strong guide cable is permanently attached to the capsule containing the radioactive source. The purpose of the cable is to safely move the capsule from its storage safe to the tumor site and back again.

In use, the doctor inserts a catheter such as a hollow plastic tube into the patient's body. A mechanical computer-controlled delivery system called an afterloader is then used to remotely remove the radioactive capsule from the safe and move it through the catheter to the tumor site. The remote afterloading technique reduces the radiological risk to medical personnel of exposure to the high-activity source capsule. In our case, the radioactive source is a miniature californium-252 neutron source.

At least three remote afterloading systems are on the market in this country for iridium-192 gamma sources. Remote afterloading systems have been designed for californium-252 brachytherapy, and these are in use in Russia, China, and the Czech Republic. No californium-252 remote afterloading systems are currently in use in the United States. Over 6000 patients have been treated worldwide using californium-252 neutron brachytherapy, and improved patient survival rates have been noted for several types of tumors relative to conventional therapies. These improved treatment statistics result from radiobiological advantages inherent in the cell-killing properties of neutrons.

A crucial aspect of remotely movable radioactive sources is the attachment of the source capsule to its guide cable. The attachment must be small, have high attachment strength, and be highly reliable. It is readily understood that the integrity of the attachment is essential to the safe operation of the movable brachytherapy source. A weak or flawed attachment can result in the separation of the source from the cable, a potentially dangerous situation for the patient and medical personnel. The force needed to pull the source capsule off the cable is called the pull strength. Pull strengths of somewhat more than two pounds have been required in the past. However, it is becoming recognized that greater pull strengths are needed to ensure safety, and also for reliability reasons.

Normally, the construction of a stronger cable attachment would increase the diameter of the capsule/cable region, and would also likely increase the total inflexible length of the capsule/cable region. Thus, these two very important aspects of capsule/cable fabrication, namely capsule/cable diameter reduction and total inflexible length minimization, would normally be compromised by attempts to strengthen the cable attachment. Some examples of prior technology follow.

Van't Hooft E., et al, "Capsule for Radioactive Source", U.S. Pat. No. 4,861,520, Issued Aug. 29, 1989 describes a machined capsule with one open end and a cable attached at the other end. After the insertion of the tiny radioactive source, an elongated plug is welded at the capsule's open end by laser or an electron beam is used to seal the capsule. This design shortens the total length of the capsule and welds, and also minimizes the total inflexible length. This is a significant advantage when threading the source capsule through the curved paths of the body to the treatment site.

Halpern D., "Neutron Brachytherapy Device and Method", U.S. Pat. No. 6,352,500, Issued Mar. 5, 2002 describes a miniature californium-252 neutron source. This more recent reference employs a californium-252 source, and uses a cable with a solid cable end. It employs various capsule/cable attachments including welds, screw threads without welds, and ordinary crimping.

Our invention is a modified crimp attachment for the capsule and cable. By crimping we mean inserting the end of the guide cable into a receiving cavity in the capsule body, and then applying external pressure in a prescribed manner to the part of the capsule that surrounds the cable end. The applied pressure deforms the capsule material, pressing it onto the cable end. In our invention, the deforming capsule material is pressed onto circumferential grooves that have been carefully micromachined into the cable end. The result is an interfacial fit that strongly resists cable detachment from the capsule. This manner of crimping the capsule to the cable end without the use of welds results in an extremely strong capsule/cable bond. Our construction has the further advantages of significantly reducing the inflexible length of the capsule/cable bond, and allowing smaller capsule/cable diameters to be used. The cable attachment is particularly well adapted for use with capsules such as those described by Halpern, above.

BRIEF SUMMARY OF THE INVENTION

It is a first object of the invention to provide a capsule/cable attachment without welds, thereby causing no heating of the surrounding metallic structure, and inducing no dimensional variability in the final product from a welding process.

It is another object of the invention to produce a solid cable end that is micromachined with pointed circumferential grooves to maximize the strength of a capsule/cable crimp.

It is another object of the invention to provide a capsule/cable attachment having greater strength than the cable itself.

It is another object of the invention to provide a capsule/cable attachment that minimizes the capsule/cable diameter.

It is a further object of the invention to provide a capsule/cable attachment that reduces the inflexible length of the capsule/cable bond.

In a preferred embodiment, a brachytherapy device comprises a guide cable having a solid cylindrical end. The solid end has a plurality of circumferential grooves machined in its cylindrical surface. The device also includes a capsule for containing a radioactive source. The capsule has a crimp region, and the crimp region includes a smooth-walled cylindrical cavity for receiving the solid cylindrical end of the guide cable. The capsule is compressed in the crimp region upon the circumferential grooves until the cylindrical cavity wall deforms around the circumferential grooves to form a high tensile strength bond with the grooves.

DETAILED DESCRIPTION OF THE INVENTION

In an early embodiment of the invention, a nonradioactive source capsule was fabricated with a cylindrical cavity machined into one end. The guide cable was an aircraft cable comprised of braided strands of wire with the cable end fused and machined into a short solid metal cylinder. The machined cable end was fully inserted into the cavity and crimped in place using a hand crimper. Evaluations of the pull strength of the bond showed that the hand crimper could only do a fair job in that the crimp did not hold as well as desired. Just as important, the hand crimper was unable to compress the source capsule into a uniformly circular cross-sectional shape needed for the subsequent insertion of the radioactive source in the other end of the capsule.

Figure 1:
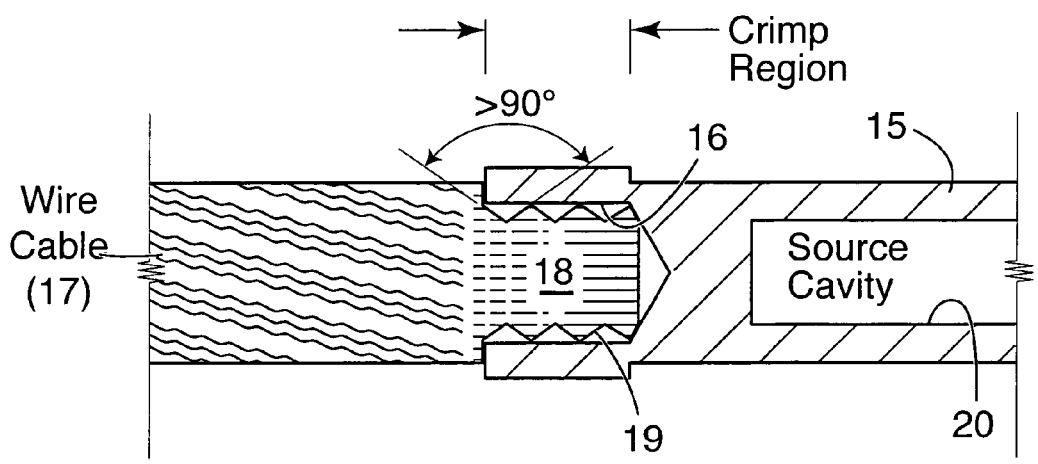
FIG. 1 is a cross-sectional diagram illustrating a capsule/cable attachment in accordance with the invention.
Figure 2:
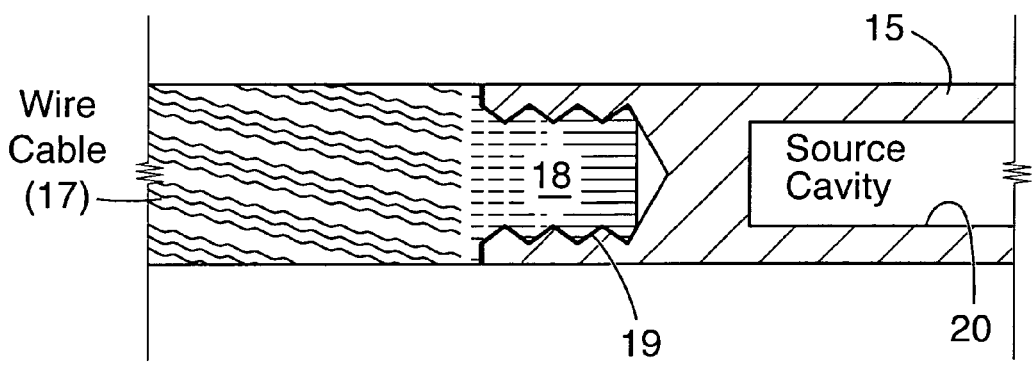
FIG. 2 is a diagram illustrating the attachment of FIG. 1 after completion of the crimping process.

A preferred embodiment of the invention is shown in FIGS. 1 and 2. In FIG. 1, a nonradioactive source capsule 15 is fabricated with a cylindrical cavity 16 machined into one end for receiving a guide cable 17. The guide cable 17 is an aircraft cable comprised of braided strands of wire with the cable end fused and machined into a short solid metal cylinder 18.

A series of circumferential grooves 19 of precise depth and spacing are micromachined in the solid cylindrical cable end 18 before crimping. The grooves 19 are individual circumferential grooves, not screw threads. The grooves 19 are micromachined using an angular cutting tool, not a rounded one. The grooves 19 are cut in such a manner that each groove adjoins, i.e., lies next to and contacts its nearest neighbor. The effect of machining the grooves in this manner is shown in FIG. 1 where the series of individual grooves have a pinking shears appearance when viewed in cross-section. With the grooves 19 cut in the solid cable end 18, the cable end of the capsule (crimp region in FIG. 1) is compressed onto the grooves 19 in a series of crimping steps. The result after crimping is shown in FIG. 2. It will be seen that the capsule 15 and cable 17 have the same uniform outer diameter.

In a preferred embodiment, the hand crimper was replaced by a pneumatically operated collet fixture. The air-activated collet jaws (three in number) were used to apply pressure to the crimp region of the capsule. The collet fixture can be readily implemented in the hot cell, where all operations involving the radioactive source must be performed remotely, including the capsule/cable attachment of the invention.

The following pressurization sequence was found to be successful in compressing the source capsule onto the grooves of the guide cable end. After insertion of the grooved cable end 18 into the cavity 16, the crimp region of the capsule 15 was clamped at 30 psi, and the pressure increased to 60 psi while maintaining the clamp. The unit was then depressurized, the source assembly rotated approximately one-quarter turn and reinserted into the collet, and the 30 to 60 psi pressure step again initiated. During the rotation sequence, the collet was activated a total of four times. This sequence of four pressurizations per cable rotation was then repeated using pressures from 50 psi to 80 psi. This sequence was then repeated a final time with the pressure fixed at 80 psi, resulting in a uniform capsule attachment to the circumference of the cable.

Importantly, the modified crimp attachment described in the pressurization sequence above applies a uniform pneumatic pressure to the capsule to produce the high strength crimp attachment. In addition to crimping the capsule 15 onto the cable end 18, this series of steps reliably produces a cylindrical capsule with round cross-sectional outer diameter as compared to handheld four-point crimpers that are unable to produce a straight, axially aligned capsule exterior.

Cable Attachment Example

A brachytherapy source capsule such as the one shown in FIG. 1 was fabricated. The capsule had a cavity 20 for receiving the radioactive source, and a cavity 16 for receiving the cable end 18. The capsule was fabricated with an outer diameter 0.043 inches in the crimp region, and an outer diameter of 0.042 inches elsewhere. The cable had an outer diameter of 0.042 inches in both the wire portion 17 and solid end portion 18. A series of plunge cuts were machined in the solid cable end 18 to form the grooves 19. It was found that grooves 19 machined at an angle of 110 degrees produced suitable knife-edged grooves having a groove depth of 0.0015 inches. The crimping sequence also compressed the larger-diameter crimp region to a diameter of 0.042 inches to match the diameter of the capsule 15 and cable 17.

This attachment has been developed for californium-containing radioactive sources, but it could be employed for sources containing other radioactive materials. The attachment has been demonstrated on platinum-iridium alloy capsules and stainless steel capsules. Other capsule materials could be considered. The attachment has also been demonstrated for capsules having two different diameters.

The crimp bond produced by the invention described herein has been found to be stronger than the cable itself. In other words, in tensile tests where the cable and capsule are pulled to failure, the cable splays. In no full failure test did the crimp itself fail. Pull strengths over 50 pounds were observed in all instances.

While there has been shown and described what are at present considered the preferred embodiments of the invention, it will be obvious to those skilled in the art that various changes and modifications can be prepared therein without departing from the scope of the inventions defined by the appended claims.

The invention claimed is:

1. A brachytherapy device comprising:
   a guide cable having a solid cylindrical end, said end having a plurality of individual abutting circumferential grooves machined at an angle greater than 90 degrees in its cylindrical surface; and a cylindrical capsule for containing a radioactive source, said capsule having a the same outer diameter as said guide cable, said capsule also having a raised cylindrical crimp region, said crimp region including a smooth-walled cylindrical cavity for receiving said solid cylindrical end of said guide cable, said capsule compressed in said crimp region upon said circumferential grooves until said cylindrical cavity wall deforms around said circumferential grooves to form a high tensile strength bond with said grooves, and said crimp region has been compressed to the same diameter as said cylindrical capsule and said guide cable.

2. The device of claim 1 wherein the outer diameter of said capsule is approximately 0.042 inches.

3. The device of claim 2 wherein the diameter of said crimp region is approximately 0.043 inches before crimping.

4. The device of claim 2 wherein said circumferential grooves are machined at an angle of approximately 110 degrees.

5. The device of claim 2 wherein said circumferential grooves have a groove depth of approximately 0.0015 inches.

6. The device of claim 1 wherein said capsule is a platinum-iridium alloy capsule.

7. The device of claim 1 wherein said capsule is a stainless steel capsule.

* * * * *